| United States Patent [19] | [11] | 4,427,658 |
|---|---|---|
| Maubois et al. | [45] | Jan. 24, 1984 |

[54] TOTAL ENZYMATIC HYDROLYSATE FROM WHEY PROTEINS AND PROCESS OF OBTAINING THE SAME

[75] Inventors: Jean-Louis Maubois, La Barre Guibourg; Loïc Roger, Rennes; Gérard Brulé, Rennes; Michel Piot, Rennes, all of France

[73] Assignee: Institut National de la Recherche Agronomique, Paris, France

[21] Appl. No.: 329,000

[22] Filed: Dec. 9, 1981

Related U.S. Application Data

[63] Continuation of Ser. No. 162,644, Jun. 25, 1980, abandoned.

[30] Foreign Application Priority Data

Jun. 26, 1979 [FR] France ................................ 79 16483

[51] Int. Cl.³ .................. A61K 37/00; A61K 31/195; A23C 21/00
[52] U.S. Cl. .................................... 424/177; 424/319; 426/7; 426/41; 426/42; 435/68; 435/69; 435/106
[58] Field of Search .................. 424/177, 319; 426/41, 426/42; 435/68, 69, 106; 426/7

[56] References Cited

U.S. PATENT DOCUMENTS

| 3,857,966 | 12/1974 | Feldman et al. ........................ 426/7 |
|---|---|---|
| 3,970,520 | 7/1976 | Feldman et al. ........................ 426/7 |
| 4,107,334 | 8/1978 | Jolly ........................................ 426/7 |

FOREIGN PATENT DOCUMENTS

| 489111 | 12/1952 | Canada ................................. 426/41 |
|---|---|---|
| 501070 | 3/1954 | Canada ................................. 426/41 |
| 966857 | 8/1964 | United Kingdom .................. 426/41 |

OTHER PUBLICATIONS

Malkames et al.–U.S. Dept. Agricult. BDI–Inf. 118 (Mar. 1951), 4 pages.

*Primary Examiner*—Sam Rosen
*Attorney, Agent, or Firm*—Oblon, Fisher, Spivak, McClelland & Maier

[57] ABSTRACT

A total enzymatic hydrolysate from whey proteins is disclosed comprising peptidic hydrolysate with substantially no residual proteins, at least 50% of the peptides containing 2 to 5 amino acids. 70 to 90% of the nitrogen present as peptides has a number of amino acids less than 10. A process for obtaining the total enyzmatic hydrolysate is disclosed comprising hydrolysis of whey proteins with proteolytic enzyme (e.g. pancreatin), which is continued until there is no precipitable nitrogen with 12% trichloroacetic acid. Enzymatic hydrolysis may be carried out continuously. The total enzymatic hydrolysate has uses as food supplement, diet food or intensive care food, and in therapeutic nutrition.

9 Claims, 14 Drawing Figures

TOTAL ENZYMATIC HYDROLYSATE FROM WHEY PROTEINS AND PROCESS OF OBTAINING THE SAME

This is a continuation of application Ser. No. 162,644, filed June 25, 1980 now abandoned.

The present invention relates to the field of whey treatment, and more particularly to products obtained by hydrolysis of the proteins contained in whey. It relates to an enzymatic hydrolysis process utilizing an enzyme capable of proteolyzing all the proteins of the whey, preferably pancreatin. The invention is also concerned with applications and uses of the resulting products, in particular as food or medicine which must comply with specific nutritional requirements.

Whey is a well-known dairy industry by-product. Its composition is approximately that of skim milk without its casein. Acid whey is obtained by acidifying the milk either by adding an inorganic acid or by producing lactic acid (seeding the milk with lactic ferments) at a pH near the isoelectric point of the casein. The whey is recovered after separation of the curd. The addition of rennet to the milk also causes the flocculation or coagulation of the casein. The whey obtained after syneresis is called rennet whey. If the flocculation occurs at the pH of milk or at a slightly lower pH but above 5.8–6.0, the whey is called sweet whey.

Whey is therefore defined with regard to the nature of the coagulation of the milk. In the cheese industry most of the wheys are in fact mixed wheys, where one of the coagulation processes prevails over another. Sweet wheys come from cooked or uncooked pressed curds (Emmental, Gruyere, Cheddar, Cantal, Saint-Paulin). The acid whey results mainly from the fabrication of fresh curds and from casein plants. There is also a complete variety of mixed wheys resulting from the fabrication of most soft curds and marbled curds (blue cheese). The composition of the wheys may therefore vary in rather wide ranges depending on the starting milk and the cheese processing employed. All wheys contain minerals fats, an amount of lactic acid, coagulant enzymes, the most interesting fraction obviously being the nitrogenous fraction. Indeed, it is the nitrogenous fraction which essentially comprises the soluble milk proteins possessing a high biological value.

The three traditions destinations of wheys were spreading on fields, dumping in waterways and use as animal feeds. The industrial treatment of wheys has already been proposed, such as concentration and drying to reduce the costs of transportation, storage and preservation. New technologies permit selective separation, concentration and purification of the constituents of wheys and modification of their physical-chemical properties while maintaining and improving their nutritional quality. Such techniques result in the production of novel and varied products from the nutritional as well as the technological standpoint. Among such techniques "demineralization" and molecular filtration may be mentioned. The molecular size difference between proteins and fat on the one hand and lactoses and mineral salts on the other hand make them separable by filtration, particularly ultrafiltration. A protein enriched solution which constitutes the valuable whey fraction is then obtained along with a solution comprising lactose and mineral salts, known as "lactose juice".

Although in relative terms, the proteins represent a small part of the solids content of the whey (less than 12%) their main attraction is increasing the value of this by-product. The proteinaceous fraction which essentially comprises soluble milk proteins, $\beta$-lactoglobulin, $\alpha$-lactoalbumin and serum albumin and immunoglobulins is interesting by reason of its nutritional value and its functional properties.

Interesting information on milk proteins is to be found in the work by H. A. Mc Kenzie, Milk Proteins, vols. 1 and 2, Academic Press, New York, 1971. Protein concentrates resulting from wheys have a high nutritional value: see for example articles by E. Forsum, Nutritional Evaluation of Whey Protein Concentrates and their Fractions. J. Dairy Sc.57 (6) 665–670 1974; E. Forsum, Whey Proteins for Food and Feed Supplement, Protein Nutritional Quality of Foods and Feeds, Part II, Marcel Dekker Ed., I.N.C. New York, 433–470, 1975; E. Forsum, Effect of Dietary Lactose on Nitrogen Utilization of Whey Protein Concentrate and its Corresponding Amino Acid Mixture, Nutrition Reports International, 11 (5), 419–428, 1975; E. Forsum, Use of Whey Protein Concentrate as a Supplement to Maize, Rice and Potatoes. A chemical and Biological Evaluation Using Growing Rats, J. Nutrition, 105(2), 147–153, 1977.

To assess the nutritional value of a protein or a proteinaceous, nitrogenous foodstuff its essential amino acid composition is compared with a reference protein. Regardless of the selected reference protein, the composition of the whey proteins is well balanced. One finds, notably, an elevated lysine, tryptophan and threonine content, an elevated cysteine content with respect to milk and a low phenylalanine and methionine content. Moreover, it is known that the mere presence of an amino acid in a foodstuff does not necessarily mean its use is obvious for the organism. The treatment to which the product is subjected before the evaporation thereof may make some amino acids at least in part unavailable. This finding was made by C. Cheftel and H. Cheftel, Brunissement non Enzymatique, Biochimie et Technologie des Aliments, vol. 1 (3), 3 Technique de Documentation Ed, Paris, 1976.

The oldest technique for extracting proteins from whey consists of making them insoluble by a denaturing heat treatment at a pH near their isoelectric point. The obvious drawback of such a technique is it denatures the proteins. Other processes have therefore been proposed to isolate the proteins by precipitation and/or "complexation". By way of example we can cite the adsorption of proteins in an ion exchanger or the addition of chemical reagents with a view to complexation or precipitation of proteins. These various techniques have substantially remained at the laboratory level. Moreover chromatographic ion exchange processes have been suggested. Cf. B. Mirabel, Nouveau Procédé d'Extraction des Protéines du Lactoserum. Ann. de la Nutrition et de l'Alimentation, 32 (2–3), 243–253, 1978. The filtration through a gel has also been applied to whey. Such a filtration process has some drawbacks. It requires a preconcentration of proteins which should not denature at the risk of altering the resolution between the different fractions. These fractions mut then be concentrated and dried. The difficulty of carrying out this process is the reason why this technique has been of limited use.

Ultrafiltration through a membrane, given the progress which has been achieved from the standpoint of equipment as well as the understanding of the phenomena observed, has become widely used in the dairy industry for the treatment of milk [N. L. Maubois and G. Mocquot, Preparation de Fromage a partir de "Pré-fromage Liquide obtenu par ultrafiltration du lait", Le Lait, 51(508), 495-533, 1970] and also for the treatment of whey (R. I. Fenton-May, C. G. Hill, and C. H. Amundson, Use of Ultrafiltration-Reverse Osmosis Systems for the Concentration and Fractionation of Whey, J. Food Sc., 36(14) 1971. During the passage of the whey through the ultrafiltration membrane, the water, the soluble minerals, the lactose, the low molecular weight nitrogen compounds (peptides, free amino acids) and the water-soluble vitamins traverse the membrane as ultrafiltrate or permeate; on the other hand the proteins and the associated components (calcium, phosphorus), fat globules and lipaphilic elements are held back of retained and become concentrated as the aqueous phase is eliminated: they constitute the "retentate" or protein concentrate. The obtention of high purity protein concentrate requires the use of ultrafiltration as well as diafiltration. In diafiltration water or an aqueous solution containing salts is continuously or intermittently added to the ultrafiltration retentate. Simultaneously or subsequently an equivalent amount of permeate is removed. Such an operation has the effect of weakening the retentate as regards filterable elements. Other than sure nutritional qualities, the whey proteins in concentrate form possess interesting functional properties. Numerous articles exist on this subject, see for example, J. E. Kinsella, Functional Properties of Proteins in Foods: a Survey. Critical Reviews in Food Science and Nutrition, 1976.

An object of the invention is a novel use of whey proteins, particularly for human nutrition. Rapid progress in medicine and surgery permits the survival of numerous patients for which the feeding and readaptation to normal foods has become a considerable problem (progress in surgical techniques but also in intensive care). At each stage of intensive care from metabolic therapy to normal nutrition, the nutrient mixture must be strictly adapted to the requirements of the patient.

The new feeding techniques such as continuous low rate enteric feeding (see E. Levy, Alimentation Entérale Continue, Principe-Technique. Indications, Resultats. 64 (4), 235-256, 1976) permit optimum use of nutrients by their direct transport in ready condition to their place of use or action. Thus after having determined a deficient digestive function it is a matter of supplying and optionally stimulating the return to near normal activity. The industrial fabrication of such products of substitution consists in fact of reproducing in vitro the deficient function which may vary from the impossibility of ingesting, chewing, to certain enzymatic shortcomings or disorders.

Moreover it is known that the actual proteolysis of soluble milk proteins occurs in the intestines under the action of pancreatic proteases. See the reference by B. Blanc, Digestibility of Proteins, Int. Dairy Federation Commission F, Final Report, Doc. 57, 1976; G. M. Gray and H. L. Copper, Protein Digestion and Adsorption. Gastroenterology, 61(535) 1971. At the present time a great effort is being made to develop enzymatic hydrolysates which are capable to easy adsorption by the human body.

The invention relates to the obtention of whey proteins from a protein aqueous hydrolysate capable of direct assimilation by the intestinal mucous membrane and of stimulating action on the deficient enzymatic systems.

Finally a number of processes for the hydrolysis of proteins, e.g., milk proteins, are known. Acid hydrolysis in fact produces solutions of free amino acids. Acid hydrolysis destroys some amino acids. Alkaline hydrolysis preserves tryptophan but causes insolubilization which markedly diminishes the nutritional value of the initial protein concentrates.

Enzymatic proteolysis is known and has been practiced for a long time for analytical and food purposes, the main objective being to make the proteins soluble. The literature takes considerably note of the numerous uses of food grade soybean protein hydrolysates, (see D. Arai, M. Noguchi, S. Kurosawa, H. Kato, M. Fujinaki, Applying Proteolytic Enzymes on Soybeans, 6-Deodorization Effect, 1970; on fish proteins see P. Hevia, J. R. Whitaker and H. S. Olcott, Solubilization of a Fish Protein Concentrate with Proteolytic Enzymes, J. Agri. Food Chem., 24 (2), 383-385, 1976; or with colza by vegetable, microbial or animal proteasis.

The application of these techniques to milk proteins on an industrial scale remains, however, very limited. The enzymatic proteolysis does not have the drawbacks of chemical methods. The conditions of hydrolysis are moderate and thereby preserve the nutritional quality of the products.

In general hydrolysis produces peptides having a pronounced bitter taste. This features limits the use of hydrolysates as human food. The degree of bitterness of the hydrolysate chiefly depends on the nature of the protein substrate and the specific nature of the enzymes. To eliminate the bitterness it has been suggested to use the action of exopeptidase. See, for example, S. Arai M. Yamashita, H. Kato, M. Fujimaki, Agri. Biol. Chem., 34(729), 1970, and K. M. Clegg, G. Smith, and A. L. Walker, Production of Enzymatic Hydrolysate of Casein on a Kilogram Scale, J. Food Technol. 9 425-431, 1974. It has also been proposed to modify the peptides by the addition of glutamic acids before a plastein reaction. It is also possible to eliminate the hydrophobic amino acids.

Nevertheless all of the known techniques are unsatisfactory and cannot satisfy the requirements of the invention. Indeed, a thorough solubilization resulting from the use of exopeptidase increases the content of free amino acids and more particularly arginine, lysine, tyrosine, valine, phenylalanine, methionine and leucine which has the direct effect of overloading the transport systems at the intestinal varrier with free amino acids and therefore causing a lesser nutritional efficiency of the hydrolysates. Moreover, the intrinsic quality of the hydrolysates is altered because the amino acid balance itself is changed which necessitates a supplementing of free amino acids.

By way of an example of a reference illustrating the state of the art U.S. Pat. No. 2,180,637 may be cited. This patent discloses a process for producing purified amino acids from certain protein fractions, milk casein being preferred. The process may comprise an enzymatic hydrolysis in a basic medium and furnishes a mixture of undenatured pure amino acids. Among the enzymes which may be used, pancreatic enzymes are cited. Such hydrolysis produces free amino acids as expressly indicated in the description of U.S. Pat. No. 2,180,637. The object of the process disclosed in this patent is to furnish protein hydrolysates containing a maximum proportion of free amino acids owing to a total hydrolysis which be must accomplished over a prolonged contact time between the enzyme and the substrate. The resulting product is therefore not necessarily devoid of enzymes. Further, the composition of the product obtained according to U.S. Pat. No. 2,180,637, by reason of its free amino acid composition is not suitable for certain fields of application such as intensive care and therapeutic nutrition for human beings. Recent studies have in fact revealed that it is appropriate to use mixtures of peptides rather than free amino acids (see, for example, D.B.A. Silk in Peptide Transport and Hydrolysis, CIBA Foundation Symposium, Elsevier Excerpts Medica North. Holland, 50, 1977). The administration of products essentially comprising free amino acids is therefore advised against by reason of the drawbacks it may have during clinical application owing to the fact that the free amino acids are not immediately assimilable and without danger for the human body (see, for example, D. M. Matthews, Intestinal Adsorption of Peptides, Physiological Review, 55(4), October 1975). Modern studies indicate that the "osmolality" of the products must be taken into account, and it is known that the osmolality of peptidic products are much less than that of corresponding products comprising free amino acids. The lower the osmolality the greater the immediate assimilability by the human body. There is therefore a need for products which are immediately assimilable, without danger for the human body, and which may be suitable, for example, for therapeutic or intensive care nutrition.

To the knowledge of the applicants it has never been proposed to obtain total enzymatic hydrolysate utilizing whey proteins and to use them directly for the specific requirements of human nutrition.

From the technological standpoint, enzymatic hydrolysis most often calls upon a batch type reactor system. The enzyme is added to a proteinaceous solution to be treated. After a shorter or longer residence time under conditions favorable to enzymatic activity and attacking the substrate, the pH is modified and a mild heat treatment inactivates the enzyme. Centrifugation may be used to eliminate the indigested insoluble fraction. But according to a batch type enzymatic hydrolysis reaction technique it is difficult to use an elevated enzyme/substrate ratio. Now, it is known, see R. C. Robins, Effect of Ratio of Enzymes to Substrate on Amino Acid Patterns Released from Proteins in Vitro, Internat. J. Vit. Nutri. Res., 48, 44–52, 1978, the decisive influence of the enzyme/substrate ratio has on the nature of the free amino acids and the free peptides during proteolysis. With a discontinuous or batch process the enzymes must be destroyed at the end of hydrolysis when they are in excess which would make it absolutely necessary with the aforesaid elevated ratios.

It has also been proposed to use fixed enzyme reactors. These, however, have appreciable drawbacks from the practical point of view. In fact, optimum enzyme activity condition in particular pH conditions, vary with time so that the operation of the reactor does not operate satisfactorily constantly. Bacteriological problems have also been found, the clogging of the fixation beds and the absorption of the proteins on the support in the case of treatment by whey. Further, the enzymatic reaction has a tendency to become inhibited with time by reason of the formation of the enzyme-protein fragment complex. Inhibition may also be due to the nature of the substrate. It is moreover very difficult to use multi-enzyme systems by reason competitive phenomena of the enzyme with respect to the substrate and of the different stabilities of the enzymes with time.

The invention takes advantage of already known means in certain other applications which consist in making use of membrane enzyme reactors. Reference is made to the article by C. Cheftel, Solubilisation Enzymatique Continue du Concentré Protéique de poisson. Essai de recyclage des enzymes. Ann. Technol. Agri., 21(3), 423–433, 1972 which discloses a membrane reactor applied to the proteolysis of fish protein concentrates. The ultrafiltration membrane retains the enzyme in solution in the reactor as well as the proteinaceous substrate. Only the products of hydrolysis, the peptides, are eliminated as they are formed. However, in practice, operation of such a reactor is not easy as Cheftel underscores. The substrate must been entirely solubilizable by the enzyme and the proteinaceous solution must be of faultless bacteriological quality.

Such is the state of the art with regard to increasing the value of whey proteins, in particular by enzymatic hydrolysis. In summary it may be said that none of the references known by the applicants has proposed a total enzymatic hydrolysate whey protein, able to be used for specific requirements of human nutrition.

In its most general aspect the invention has an object a total enzymatic hydrolysate of whey proteins comprising a peptidic hydrolysate which contains practically no residual proteins and of which at least 50% of the peptides contain 2 to 5 amino acids.

According to a preferred mode of carrying out the invention the above-mentioned hydrolysates contain 70–90% nitrogen in the form of peptides having a number of amino acids less than 10.

According to another aspect of the invention there is provided a process for obtaining such hydrolysates from whey proteins, consisting of putting the proteins into contact with a proteolytic enzyme capable of simulating proteic digestion which occurs in vivo in the human body, the enzyme preferably being pancreatin, the hydrolysis then being conducted until the product no longer contains any residual proteins, i.e. no nitrogen precipitable with a 12% trichloroacetic acid, thereafter recovering the resulting hydrolysate which represents the total enzymatic hydrolysate sought.

Preferably the invention comprises first ultrafiltering whey, the retentate of ultrafiltration being brought into contact with a proteolytic enzyme capable of simulating proteic digestion which takes place in vivo in the human body, the enzyme preferably being pancreatin, the hydrolysis being continued until the product no longer contains any residual proteins, i.e., no precipitable nitrogen with a 12% trichloroacetic solution, thereafter recovering the resulting hydrolysate which represents the total enzymatic hydrolysate sought.

As mentioned above, such a process is advantageously carried out in an apparatus which combines ultrafiltration equipment with a membrane enzyme reactor thereby permitting continuous operation. Owing to such a combination and to the choice of the parameters of the reaction which are adapted to the treatment of whey proteins the invention provides a total enzymatic hydrolysate of the said proteins. Heretofore the hydrolysis have only been partial and by this very fact the resulting products did not fulfill the requirements of the present invention.

Nearly all the resulting peptides comprise 2 to 5 amino acids whereby the product according to the invention satisfies specific nutritional requirements. The free amino acids represent 10–15% of the nitrogen fraction in general. The basic amino acids (arginine and lysine) and aromatic amino acids (tryptophan, phenylalanine, tryosine) and leucine comprise the essential part of the free amino acids. The examples hereinbelow demonstrate the compositions of certain categories of hydrolysates given by way of example.

The similarity of the amino acid composition of the flocculation fraction and of the floating fraction obtained during concentration by evaporation of 100 g per liter of the hydrolysate leaving the reactor, indicates a uniform distribution of the hydrophobic and hydrophilic properties between the different classes of peptides. The concentration operation may be continued until reaching an elevated solids content which may attain up to 25% before spray drying.

The hydrolysates obtained which come from milk proteins are recognized as having an excellent biological value. They therefore fulfill the nutritional requirements of patients suffering from pancreatic insufficiencies or of metabolic patients. The invention therefore has a direct application in dietetic foods perfectly assimilable by the human body since they are capable to passing through the intestinal barrier and therefore conveniently digested and assimilated. One of the aspects of the invention therefore concerns an intensive care food containing, as an active ingredient, a product of the invention based on a total enzymatic hydrolysate of whey proteins possibly in combination with a neutral vehicle suitable for oral feeding or enteral administration.

By way of a starting material for the process according to the invention any whey may be used. For example, a whey of industrial origin may be used, in particular mixed wheys resulting from mixing of wheys of different cheese fabrications. Whey may be used which is prepared from raw or heat treated milk by lactic or rennet precipitation. Yet, as a variant, a reconstituted whey may be used. Original whey may be heat treated after skimming, for example, at a temperature of the order of 58° to 60° C. It may then be concentrated by evaporation. The preconcentrate is then optionally diluted to prevent excessive crystallization of the lactose and kept at a temperature of the order of 4° C. It is convenient to use whey protein concentrates reconstituted from a powder.

The process according to the invention applies to whey proteins regardless of the method by which they were produced. Thus, whey proteins may be isolated by any known means before being subjected to enzymatic hydrolysis. The proteins may, for example, be made to coagulate when heated. But preferably the proteins are obtained by ultrafiltration of whey because this operation does not cause whey denaturation various reasons, e.g., economic, the process according to the invention may be successfully applied to proteins precipitated by heat from the whey.

The whey or the preconcentrate is advantageously purified by ultrafiltration and by diafiltration. The different retentates are then dried, e.g., spray dried.

During ultrafiltration techniques known to those skilled in the art are used such as they are illustrated in the references cited at the beginning of the description. The obtention of a high purity protein concentrate is, in general, effected in two stages: simple ultrafiltration followed by diafiltration. The ultrafiltration membranes are conventional: they are the ones known for retaining or holding back all soluble whey proteins. Their cut-off capacity is generally between 500 and 50,000. The membranes may be of any nature. They may be inorganic membranes as well as organic membranes. By way of example of organic membranes, membranes of the following materials may be used: polyolefin, polyacrylonitrile, polyvinyl chloride, cellulose acetate, polycarbonate or other similar materials. By way of example of inorganic membranes any kind or porous substrate satisfying the foregoing definitions may be utilized. All these concepts are well known to those skilled in the milk or whey ultrafiltration and therefore need not to be explained in greater detail.

The best results have been obtained with membranes available on the market under the trade name "Nuclepore". Such membranes are described in the brochure entitled "Basics of Filtration and Separation" by H. W. Ballew, Nuclepore Corporation, 1978. These membranes comprises a film of polycarbonate irradiated by ion bombardment. The pores are well defined cylindrical holes with a diameter precision of ±15%. These microfiltration membranes not only have the capacity of eliminating insoluble proteinaceous, lipidic or lipoproteic products, but also are able to reatain or hold back microorganisms and exert a supplementary sterilizing function.

In practice, in order to achieve optimum conditions of ultrafiltration of whey, the pH is adjusted to a value, generally between 6 and 7, to take into account the origin of the whey (acid coagulation or rennet coagulation). The adjustment of the pH may substantially improve the performance of the apparatus. The improvement is enhanced when the adjustment of the pH occurs after preheating the whey to 80° C. for 15 seconds (see J. F. Hayes, J. A. Dunkerly, L. L. Muller, and A. T. Griffin, Studies on Whey Processing by Ultrafiltration II. Improving Premeation Rates by Preventing Fouling. The Australian L. of Dairy Tech., 38(3), 132-140, 1974. Further, the elimination of some minerals improves the permeation rates. Likewise, the passage of the whey accross an ultrafiltration membrane whose cut-off threshold is above the molecular weight of the native proteins eliminates the microorganisms, the casein fines, the soluble proteins in aggregate form. This prefiltration of whey augments the permeation rate: see the works by D. N. Lee, and R. L. Merson, Chemical Treatments of Cottage Cheese whey to Reduce Fouling of Ultrafiltration Membrane, J. of Food Sc., 41, 778-786, 1976 and D. N. Lee and R. L. Merson, Prefiltration of Cottage Cheese whey to Reduce Fouling of Ultrafiltration Membranes, J. of Food Sc. 41, 403-410, 1976. These authors have found that the addition of an inorganic salt such as calcium chloride or sodium chloride improves the ultrafiltration rate. This treatment may be contemplated during the diafiltration operation with a view to obtaining very pure protein concentrates under optimum conditions.

In conformity with an advantageous form of carrying out the invention the step of ultrafiltration of the whey is combined with the step of enzymatic hydrolysis of the ultrafiltration whey retentate. Regardless of the manner of obtaining the whey proteins the enzymatic hydrolysis is carried out continuously by introducing protein concentrate into a reaction zone with a view to intimately contacting it with the enzyme, the products of reaction are drawn off by bringing them from the reaction zone to an ultrafiltration zone where a permeate is continuously drawn off which constitutes the peptidic hydrolysate constituting the product sought according to the invention, the reaction being continued until the permeate is a total enzymatic hydrolysate, recycling may be provided from the ultrafiltration zone to the reaction zone.

For reasons related both to the good operation of the reactors and to the destination of the final products, the elimination of the nonprotein compounds of the whey must be as high as possible. It is there appropriate that the aforesaid ultrafiltration retentate have a protein solids content ratio as high as possible. For this reasons in particular diafiltration has been proposed after ultrafiltration. In this case, however, where the pressure of a small amount of residual lactose may be present this may cause several disadvantages to the composition of the final product, the hydrolysis of this sugar may be effected. Tests have shown that the preliminary enzymatic hydrolysis of the whey protein concentrates have no detrimental consequence on the rest of the protein hydrolysis process. We will now give indications as to the parameters of the enzymatic reaction which have a great importance for the obtention of a total enzymatic hydrolysate.

In the first place the pH of the reaction zone must be adjusted between 7 and 9 taking into account the nature of the enzymes used, which must be capable of totally digesting the whey proteins in the conditions of digestion of a human body. By way of enzymes preferably pancreatin is used which is a complex mixture containing trypsine, chymotrypsine and other proteolytic enzymes. In practice a readily commercially available pancreatic extract will be used. Yet, if necessary, enzymes resulting from a synthetic mixture may be utilized the composition of which approximates that of pancreatin. Such mixtures will therefore essentially contain trypsine and chymotrypsine, if necessary with other secondary enzymes present in the natural pancreatic extract. If has been found according to the invention that at the pH between 7 and 9 and preferably between 7 and 8.5 the pancreatin and the other similar enzymes satisfying the requirements of the invention had maximum stability.

It is appropriate to observe rather strict temperature conditions in the enzymatic reaction zone. Indeed, it has been found that the activity of the enzymes were more influenced by the temperature than by pH. Test have shown, according to the invention, that with trypsine the maximum temperature in the reaction zone must not be greater than 54° C. and with chymotrypsine this temperature must not exceed 45° C. In practice when pancreatin is used a compromise will therefore be struck taking into account the optimum conditions of the intestinal proteolysis (temperature between 37° and 40° C.) and owing to the fact that a higher temperature is less favorable to the development of germs and permits greater ultrafiltration rates to be obtained. For the needs of the invention temperatures of the order of 40° C. have been found suitable.

Obviously the pH and temperature reaction parameters are related. Thus, the ranges of pH of 7.5 to 8.5 for temperatures of the order of 40° to 45° C. are suitable.

Another important parameter in the reaction zone is the ratio of enzyme concentration to protein concentration. This ratio must be high as in the case of in vivo protein digestion. In the case of pancreatin the pancreatin substrate ratios of the order of 8 to 15%, in particular of the order of 12%, have yielded appropriate results.

All the above parameters were selected so that all the proteins are proteolyzed. This avoids increasing their concentration as a function of time in the reaction. Moreover, the protein solution supplying the enzymatic hydrolysis reactor must not contain nonprotein components capable of being retained by the membrane. The enzyme must also be effectively retained by the membrane. Finally, as products intended for consumption are involved, the operating conditions must not promote microbial growth.

To achieve optimum enzymatic hydrolysis it is appropriate to select carefully the ultrafiltration membrane to be used in relation to the enzymatic reactor. The membranes used are of any type, organic or inorganic. They may be in the form of modules as it is known in this kind of apparatus. The construction of membranes which have given good results is that of hollow fiber modules. By way of illustrative example, membranes commercially available by Amicon under the trade name H10 P 5 (cut-off capacity 5000) and H10P10 (cut-off capacity 10,000) as well as membranes commercially available through Romicon under the trade name PM 2 (cut-off capacity 2,000) or PM 50 (cut-off capacity 50,000) may be used.

It is important to select a membrane which, in operation, may satisfy the requirements of the present invention and in particular efficiently retain the enzyme and have satisfactory performance, especially as regards service life. Indeed, the raw material treated, i.e., the protein solution resulting from whey may contain components which are detrimental to good operation of the membrane. In the course of the process of obtaining whey, an insoluble protein fraction may be present because of the usual heat treatment, 72° C. for 15 seconds. That is the reason why it is preferable to remove this protein fraction beforehand by high speed centrifugation. The whey may also contain a fraction essentially comprising lipides and lipoprotein complexes. These components, althrough of elevated molecular size, are not centrifugeable. The accumulation in front of the membrane in relation to the enzyme reactor may limit the operation of the reactor.

According to a preferred embodiment of the invention membranes are employed whose hole contours are well defined.

In another respect, the ultimate use of the protein hydrolysates according to the invention requires that the products entering the reactor be of good biologically healthy grade. The widespread addition of potassium nitrate to milk used in the manufacture of pressed cheese may mean that the whey which is a by-product of this process is rejected or must undergo a supplementary demineralization treatment by electrodialysis or in an ion exchange reactor if the residual nitrate content is deemed unacceptable.

The presence of hydrogen peroxide, which is the antiseptic widely used in the bacteriological stabilization of whey, is also not acceptable.

On account of its method of fabrication and its composition (low fat content and small bacteria population) the whey which is a by-product of the fabrication of casein using mineral acids is a preferred starting material for the process according to the invention.

As mentioned above, it is important to maintain in the reaction zone a basic pH of the order of 7 to 9 with a view to permitting total digestibility of the protein concentrate. To this end there is continuously or intermittently introduced into the reaction zone a basic compound which may be sodium hydroxide or carbonate, potassium hydroxide or carbonate, calcium hydroxide, ammonium hydroxide or a mixture of these compounds. The choice of the particular basic compound will depend on the ultimate use of the end product, the sodium, potassium, calcium or ammonium ion content in the product being the determinant criterion for the choice.

One skilled in the art will therefore have at his disposal various parameters in order to obtain the best results and accomplish total enzymatic hydrolysis of the whey proteins. It will also be noted that the particular values to be chosen may depend on the size of the enzyme reactor as well as the nature of the equipments used.

It is appropriate to conduct the hydrolysis of the whey protein until enzymatic hydrolysates are obtained which contain no detectable proteins. Then the hydrolysate is brought into contact with the membrane of the ultrafiltration enzyme reactor module.

The process according to the invention may be carried out in two separate steps: a first step consisting of enzymatic hydrolysis and a second step consisting of ultrafiltration. The equipment for carrying out each of these steps may be separate or integrated. Yet, as a variant, the process may also be performed continuously, the above two steps being carried out in a single apparatus. During the first moments of operation, e.g. during about one hour, the permeate (the liquid permeating through the membrane) is recycled in the hydrolysis zone in order to obtain the desired hydrolysis content of whey proteins. When total hydrolysis is reached protein concentrate to be treated is introduced into the reactor at a rate identical to that of the permeate. In the particular operating conditions involving a temperature of about 40° C., a pH held at 8.0 in the reaction zone, a protein content of about 80 g per liter of solution feeding the reactor and a pancreatin/substrate ratio of about 12%, the total "continuous" operating period is of the order of 7 to 8 hours.

It will be observed that a preliminary heat treatment of the concentrated whey protein solution will not improve its overall digestibility.

Among the proteins present in the proteolysed concentrate solution the serum albumin is the one which is hydrolyzed with the greatest difficulty with the pancreatin.

The products according to the invention may have numerous applications or uses in the field of nutrition and therapy. The products according to the invention are of a nature to trigger, by action on intestinal receivers, the secretion of internal pancreatic hormones (insulin and glucagon, for example) and trigger the secretion of gastro-intestinal hormones (gastrin, gastric inhibitor polypeptide, for example).

The products according to the invention may be used with a view to therapeutic nutrition or as an intensive care medicine, they ameliorate the digestive disorders of a resected intestine so as to achieve nutritional autonomy after a certain period of time and thereby stop tube-feeding the patient. More generally the products according to the invention may be used with a view to therapeutic nutrition or as a medicine in the treatment of digestive infections such as for example gastritis, peptic ulcers, ileitis, insected intestines and colitis.

The present invention is also concerned with pharmaceutical compositions containing a product according to the invention mixed with usual excipients.

Taking into account the physical form of the novel product (a powder soluble in an aqueous medium) the form of presentation does not give rise to any problems. The novel products may be ingested or administered as such by the enteral tract, for example, by mixing with a customary food. They may also be presented in the form of compositions with common excipients, for example, suitable for oral administration. The appropriate compositions for the purposes of the invention may thus be presented in the form of a pill or a capsule with known excipients such as talc, magnesium stearate, finely divided silica or any other similar vehicle known to those skilled in the art.

The invention will now be illustrated by means of examples. Of course, these examples are in no way limiting. In the following example use will be made of apparatus described with reference to the accompanying drawings, in which.

Figure 1:
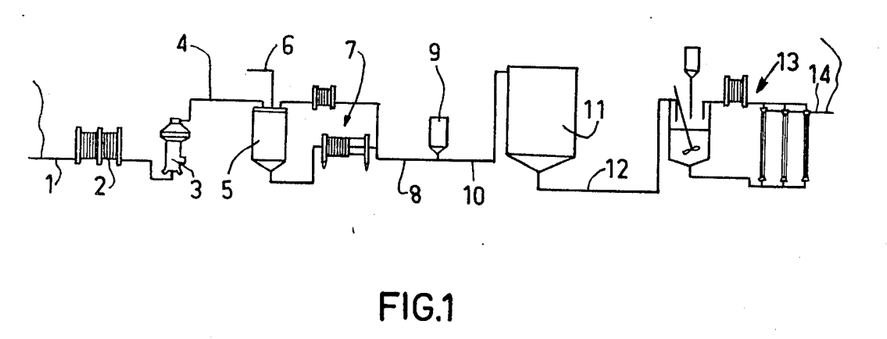
FIG. 1 represents a general schematic view of the apparatus.

As represented in FIG. 1 the apparatus comprising an ultrafiltration unit and an enzyme reactor. The whey is introduced via line 1 first through a temperature exchanger 2 and a centrifugal separator 3 before being introduced into the ultrafiltration module per se. The heated whey with centrifugeable insolubles removed is introduced via line 4 into a tank 5 at the same time as the water is supplied by line 6. The water is used continuously for diafiltration. The ultrafiltration module per se is designated by general reference numeral 7. Retentate or concentrate held back by the ultrafiltration membrane is recovered in line 8. Means are designated at 9 for adjusting the pH of the retentate as well as its concentration. Once these steps are completed the retentate is conveyed via line 10 and introduced into a buffer tank 11 from which it is drawn for hydrolysis in the enzyme reactor. To this end the whey passes via line 12 connected to the buffer tank 11 to the enzyme reactor designated by general reference numeral 13. The hydrolysate which constitutes the final product sought is recovered at line 14.

For specific tests the whey or preconcentrate was ultrafiltered in a DDS module having a surface of 9 sq.m. equipped with BR 6 P membrane commercially available through De Danske Sukker Fabrik, the ultrafiltration operation being carried out in batches at a temperature of 50° C. The various retentates obtained by ultrafiltration alone or with diafiltration were spray dried.

Figure 2:
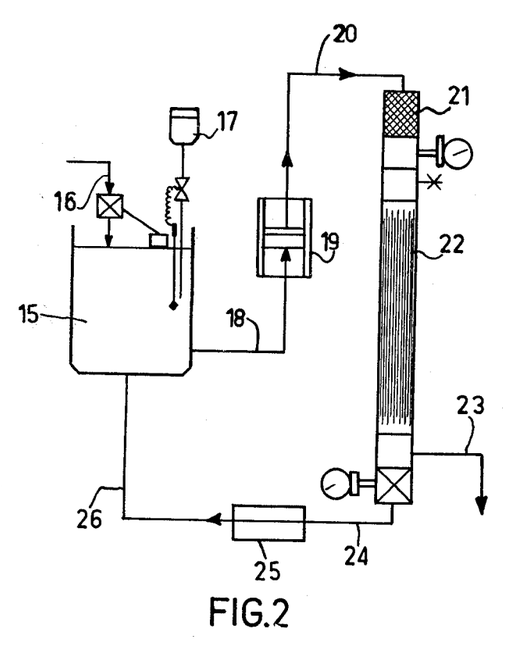
FIG. 2 is a flow diagram representing the membrane enzyme reactor used in the apparatus of FIG. 1.

FIG. 2 represents the membrane enzyme reactor. It comprises, first of all, a reaction vessel designated by general reference numeral 15. Continuous supply of whey proteins is effected via line 16. An apparatus 17 serves to meter and maintain the pH in the reaction vessel by neutralizing the H+ ions freed during the breaking of the peptide bonds. The apparatus is a pH stat Mettler comprising a voltage amplifier, an equivalence point selector and an automatic reagent dispensing burette, the reagent being a basic compound as mentioned above. No undue wear or collapse of the electrode has been found. The product of hydrolysis drawn from the reaction vessel via line 18 is carried by a pneumatic diaphragm pump 19. A practical example is an Amicon pump model LP 20A with a pumping rate of 720 liters per hour at 1.7 bars. It the discharge side of the pump the product passes into a line 20 and brought to a prefilter 21 having a porosity of 150 microns. Reference numeral 22 designates the ultrafiltration module. In the specific example the DC 10 S system of the Amicon Company is used comprising hollow fiber ultrafiltration cartridges. The permeate was recovered in line 23 and comprises the peptidic hydrolysate sought. The retentate from the ultrafiltration module 22 was drawn off by the line 24, introduced into an exchanger 25 and conveyed via line 26 to be recycled in reaction vessel 15.

The membranes used were of the hollow fiber type having the following properties:

| Type | Cut-off | Surface Area | Manufacturer |
|------|---------|--------------|--------------|
| H10 P 5 | 500 | 0.9 sq.m. | Amicon |
| H10 P 5 | 10,000 | | |
| PM 2 | 2,000 | 1.4 sq.m. | Romicon |
| PM 50 | 50,000 | | |

For the tests reported hereinbelow whey of industrial origin from a mixture of Emmental and Saint-Paulin wheys was used, its pH ranging between 6.2 and 6.4. After skimming the whey was heat treated at 58°–60° C. for about 15 seconds. It could then be concentrated by evaporation to a solids content of about 50%. This preconcentrate was then diluted 2.5 times to avoid excessive crystallization of the lactose and cooled to a temperature near 4° C. before storing overnight. As a variant, certain wheys used in the examples hereinbelow were prepared in situ from raw milk or heat treated milk by lactic or rennet precipitations.

In the usual experimental conditions the protein concentrate was reconstituted to a protein content of 100 g/l in the reaction vessel 15. The reaction temperature was set at about 40° C. The apparatus 17 measures and maintains the pH. After equalizing the temperature and adjusting the pH the extemporaneously reconstituted enzyme (pancreatin) was added. The addition of the alkaline compound was continuously recorded to maintain the pH in the reaction zone. Each batch drawn off was subjected to precipitation in 12% trichloroacetic acid proteolysis was followed while determining the floating soluble nitrogen and the freed $NH_2$ groups.

The solids content of the samples of whey, ultrafiltrate and hydrolysates were determined by drying in an oven at 102°–105° C. for 7 hours.

The nitrogen content was determined by a microkjeldahl on a Technicon autoanalyser:

The total nitrogen content was obtained by direct metering after dilution (Total Nitrogenous Material).

The nonprotein nitrogen content (NPN) was determined by metering after precipitation of the proteins in the 12% trichloroacetic acid.

The ash content was determined according to the AOAC method (AOAC Standard, 1945).

The determination of the content of mineral substances was carried out by atomic absorption in a Technitron 1200 apparatus in accordance with report by G. K. Murphy and V. Rhea, Determination of Major Cations in Milk by Atomic Absorption Spectrophotometry, J. Dairy Sc., 50,313–317 (1967) modified by Brule et al, Etude de la Teneur en Minéraux des Produits Obtenus lors de l'Ultrafiltration du Lait sur Membrane, Le Lait, 539–540, 600–615, 1974.

The quantity of free $NH_2$ groups determined by reaction with ninhydrin after alkaline hydrolysis according to Hirs et al. J. Biol. Chem. 219,1190 (1956) by means of trinitrobenzene sulfonic acid according to Fields, Biochem,J. 124,581–590 (1971).

The determination of the quantity of amino acids was carried out according to the method of Spackman et al, Anal. Chem. 30,1190 (1958). The peptides (2 mg) were hydrolyzed for 24 hours, 48 hours and 96 hours at 110° C. in vacuum sealed tubes per 1 ml of HCl 6 N, distilled twice. The results are expressed in g per 100 g of amino acids after correcting for destruction of threonine, serine, cysteine and tyrosine during hydrolysis.

The quantity of tryptophan was determined separately according to the Spies method (1957) by colorimetric reaction with paradimethyl aminobenzaldehyde, after hydrolysis with pronase.

The measurement of the optical densities at 280 nm, and at 420 nm (determination of the quantity of the $NH_2$ groups with TNBS) at 570 nm (determination of the quantity of the $NH_2$ groups with ninhydrin), or the curve of the absorption spectra of the proteins, peptides or amino acids for their identification was carried out on a Beckman type Acta VI spectrophotometer in a quartz cell having a one centimeter optical path.

The amount of residual activity of the trypsine in the peptidic hydrolysates was carried out according to the Hummel method, Can. J. Biochem. Physiol., 37,1393 (1959) by following the increase of the absorption at 247 nm due to the hydrolysis of a synthetic substance, p-toluenesulfonyl-L-arginine methyl ester (TAME).

The qualitative and quantitative determination of the soluble proteins (lactoglobulin, lactoalbumin, serum albumin) in the whey, the retentates, the ultrafiltrates, the protein concentrate before, after and during hydrolysis, was accomplished by electrophoresis in a polyacrylamide gel according to the Aschaffenburg method (see Protein Phenotyping by Direct Polyacrylamide Gel electrophoresis of Whole Milk, Biochem. Biphys., Acta. 82, 188–191 (1964), modified: the gel used was either 5% or 9% of a 1:1 mixture of acrylamide and bisacrylamide (Cyanogum:Apelab, Paris).

The plates after exposed to amido black and decoloration with 10% acetic acid were read by means of a Philips densitometer.

The separation of proteins, peptides and free amino acids according to their molecular weight was performed by filtering through Sephadex gels (Pharmacia).

As a function of the nature of the constituents to be separated the following gels were used:

| Constituents to be separated | Nature of gel | Eluent |
|------------------------------|---------------|--------|
| proteins-proteins | $G_{100}$ | Phosphate buffer pH 7.5 |
| proteins-large peptides | $G_{75}$ | Phosphate buffer pH 7.5 |
| peptides-peptides | $G_{50}G_{25}$ | 30% acetic acid |
| peptides-free amino acids | $G_{15}$ | 30% acetic acid. |

The eluents were analyzed by measuring the optical density at 280 nm and by metering the free $NH_2$ groups by ninhydrin.

The fractionation of the peptides and amino acids as a function of their isoelectric point and their charge was obtained by using cationic ion exchange resins (AG 50×W₂—Biorad Laboratory Richmond, Calif.). The peptidic hydrolysate was put into the contact of the resin in batches at different pHs. After a period of contact and settling, the floating portion was analyzed.

EXAMPLE 1

In this example an apparatus of the general type represented in FIG. 1 was used and an enzyme reactor of the type represented in FIG. 2. The whey was treated beforehand in the centrifugal separator 3 at the speed of 1000 g for 15 minutes before entering the apparatus.

The enzyme used was pancreatin commercially available under the trade name SIGMA, of bovine origin having an activity of 4 NF (French standard). The reaction conditions in the reaction vessel of the enzyme reactor were as follows:

| | |
|---|---|
| temperature | 40° C. |
| pH held at | 8.0 |
| protein content in solution supplying reactor | 80 g/l |
| pancreatin/substrate ratio | 0.12 |

Figure 3:
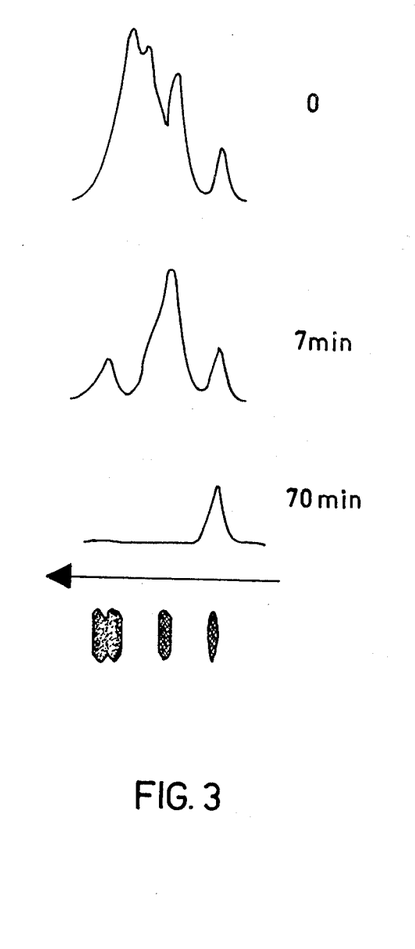

The hydrolysis of the whey proteins was followed by electrophoresis in a polyacrylamide gel. The results are illustrated in FIG. 3. This figure shows at different stages of the reaction, at time 0.7 minutes and 70 minutes, the tends of the curves of electrophoresis corresponding to the solubilization of the whey proteins. The diagram in the lower part of FIG. 3 represents the migration of the various proteins. The $\beta$-lactoglobulin is represented by the abbreviation $\beta$-lacto, the $\alpha$-lactalbumin by the abbreviation $\alpha$-lacta and the bovine serum albumin by the abbreviation BSA.

Figure 4:
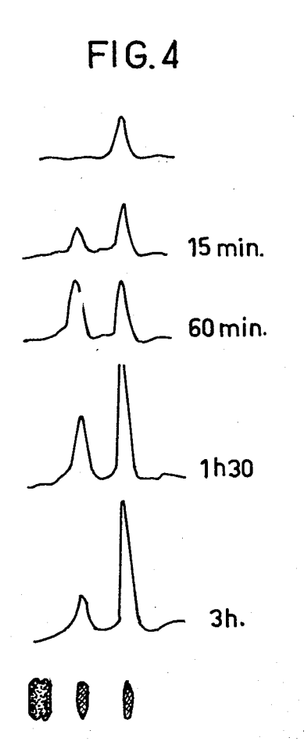

The polyalcrylamide gel may be used at a concentration of 9%. The results represented in FIG. 3 show that the speed of hydrolysis of proteins is different. The $\beta$-lactoglobulin is more quickly hydrolyzed that the $\alpha$-lactalbumin which in turn is faster than the serum albumin. The serum albumin is at least partly insensitive to the proteolysis. The bovine serum albumin of the whey cannot therefore be totally hydrolyzed. FIG. 4 is a figure similar to FIG. 3 but recording the results of the continuous operation of the reactor. The electrophoresis measurements in a 9% polyacrylamide of the continuous hydrolysis of the whey protein concentrate with pancreatin in the enzyme reactor confirms that the bovine serum albumin accumulates in the reactor.

Figure 5:
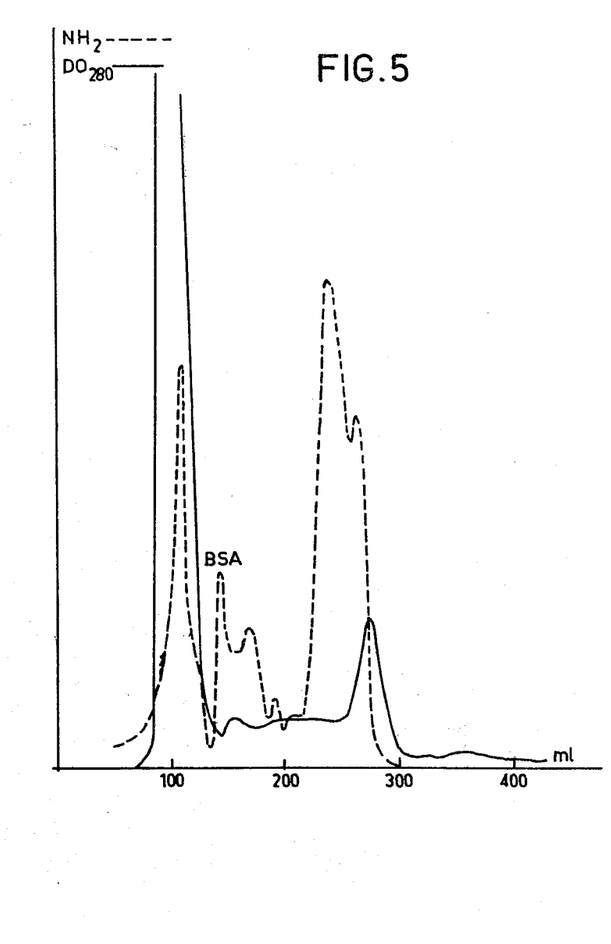

After three hours of operation of the vessel, the bottom end of the vessel was purified by diafiltration and analyzed. The results are represented in the graph of FIG. 5. FIG. 5 shows the molecular distribution of the constituents present in the enzyme reactor at the end of pancreatic hydrolysis of the whey protein concentrates after purification by diafiltration (Sephadex G-100 gel, phosphate buffer, pH 7.5). The filtration curve indicates the presence of three constituent groups:

the first, of highest molecular weight, having a high absorption at 280 nm (presence of a dip) for low $NH_2$ content;

the second, whose electrophoretic image and absorption spectrum at 280 nm correspond to that of the bovine serum albumin; and the third of low molecular weight, i.e. the peptides.

EXAMPLES 2 and 3

These examples also concern the continuous solubilization of whey proteins with pancreatin in the enzyme reactor. The operating conditions are indicated in Table 1.

TABLE I

| | EXAMPLE 2 | EXAMPLE 3 |
|---|---|---|
| Membrane Cut-off | 5,000 | 5,000 |
| Temperature | 40° C. | 37° C. |
| pH | 8.5 | 8.5 |
| Initial protein content | 84.4 g/l | 82 g/l |
| Base used | 2N KOH | 2N KOH |

TABLE I-continued

| | EXAMPLE 2 | EXAMPLE 3 |
|---|---|---|
| Enzyme/substrate ratio | 11.8% | 12.6% |
| Prehydrolysis period | 2 hours | 1 1/2 hours |
| Protein content of solution supplying reactor | 45 g/l | 50 g/l |

In the two tests, the apparent degree of hydrolysis (soluble nitrogen/total nitrogen) in the permeate was held constant owing to the small enzyme input. The length of reactor operation was from 7 to 8 hours.

Figure 6:
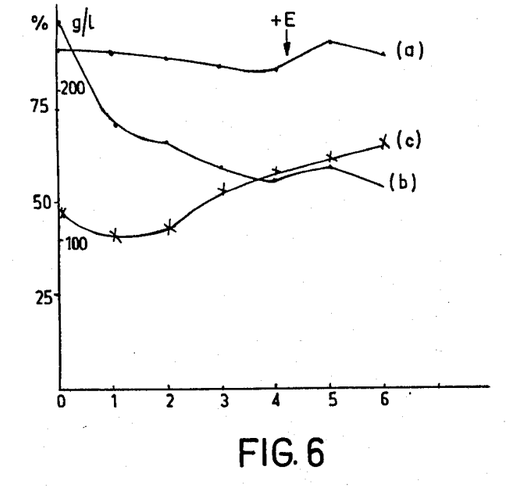
Figure 7:
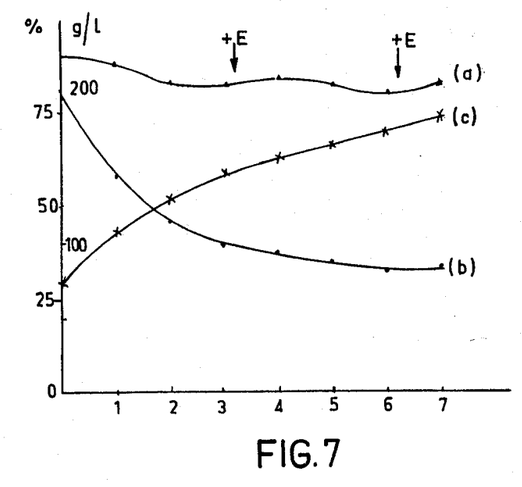

The results are best seen in the graphs of FIGS. 6 and 7. Along the abscissae is marked the reaction time in hours and along the ordinate the concentration of solids or proteins of the products considered in grams per liter. In FIGS. 6 and 7 the curves (a) and (b) respectively represent the apparent degree of hydrolysis of the permeate and the ultrafiltration retentate whereas the curve (c) represents the solids extract of the retentate.

Figure 8:
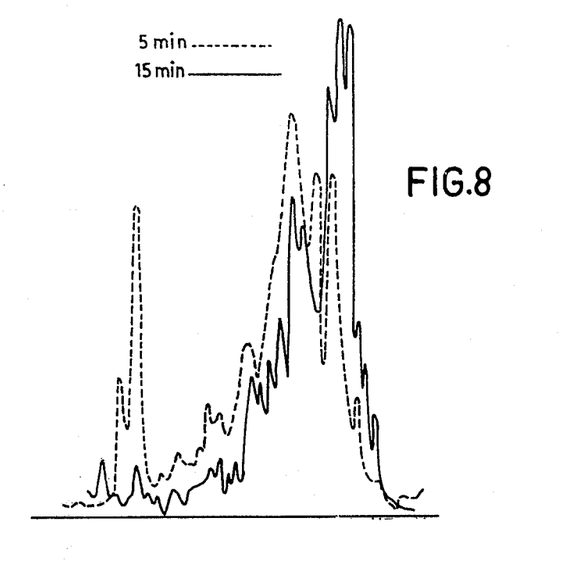
Figure 9:
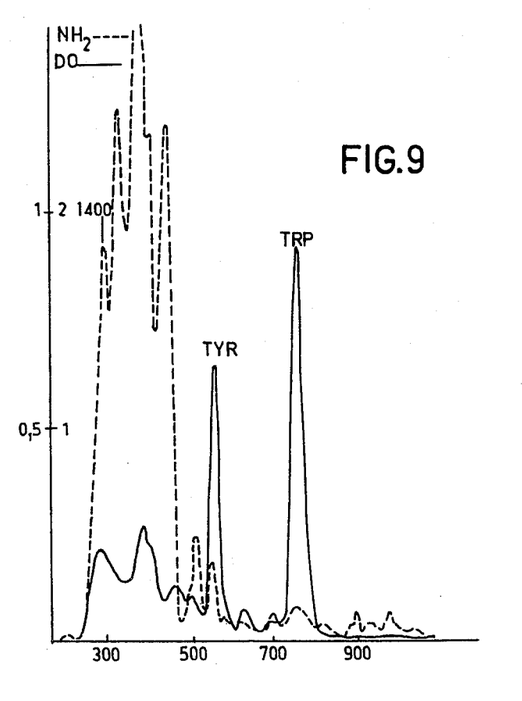
Figure 10A:
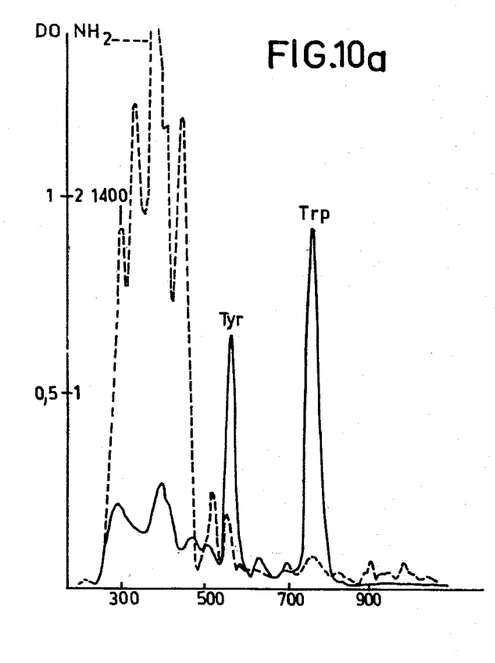
Figure 10B:
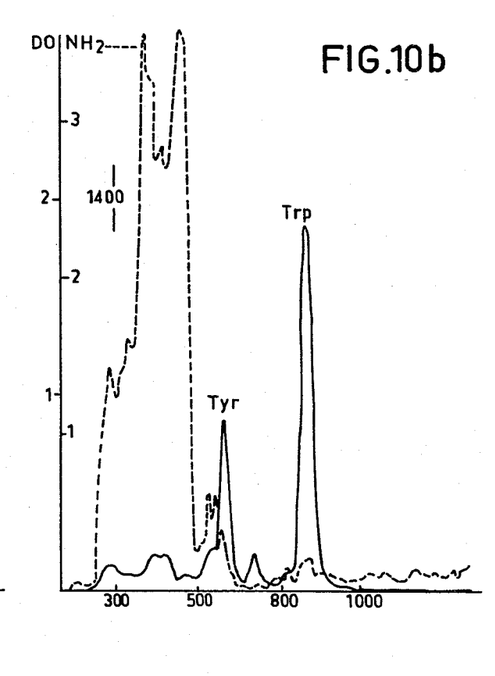

We then proceed to characterize the resultant hydrolysates. FIG. 8 illustrates the molecular distribution of the peptides obtained by pancreatic hydrolysis of a whey protein concentrate as a function of enzyme/substrate contact time. The measurements were carried out by filtering through a Sephadex G 50 gel and elution with a 30% acetic acid. FIG. 8 demonstrates the effect of enzyme/substrate contact time. FIG. 9 illustrates the molecular distribution of the peptides obtained by pancreatic hydrolysis of a whey protein concentrate after total enzymatic hydrolysis, the measurements were carried out on a Sephadex G 15 gel (elution with 30% acetic acid). As illustrated by FIG. 9 all the peptides obtained have a size less than 2,000, the majority being situated between dipeptide and decapeptide. The amount of free amino acids is small and may be assessed at an amount less than 10%. The use of various membranes having different cut-off shows there is no difference between the peptides obtained on membranes with a 5,000 cut-off and those obtained with membranes having a 10,000 cut-off. FIG. 10 shows that the passage of pancreatic hydrolysate through a 5,000 cut-off membrane with a 15,000 cut-off membrane modifies the curve of the molecular distribution of the peptides. This figure therefore illustrates the possibility of modifying the distribution of the peptides by subjecting the total initial hydrolysate obtained previously with a 5,000 cut-off membrane to an ultrafiltration with a PM 2 membrane with a cut-off of 1,500–2,000. The measurements have been carried out with a Sephadex G 15 gel (elution with 30% acetic acid).

Other measurements were carried out on the compositions of the products obtained by determining what fractions were nondialyzable and dialyzable. The cut-off with dialysis is situated at about a molecular weight of 2,000. Table 2 hereinbelow corresponds to the aminograms of the dialyzable fraction I and nondialyzable fraction II of a pancreatic hydrolysate of whey protein concentrate.

TABLE 2

| | I+ | II++ |
|---|---|---|
| Ile | 7.0 | 5.70 |
| Leu | 10.96 | 7.52 |
| Lys | 8.92 | 9.10 |
| Met | 2.20 | 2.10 |
| Cys + Cyst | 2.0 | 3.70 |
| Phe | 3.63 | 1.91 |
| Tyr | 3.03 | 5.80 |

TABLE 2-continued

|     | I+    | II++  |
|-----|-------|-------|
| Thr | 6.70  | 6.70  |
| Trp | 1.62  | 1.13  |
| Val | 6.20  | 5.40  |
| Arg | 2.72  | 2.17  |
| His | 1.98  | 1.34  |
| Ala | 5.16  | 4.19  |
| Asp | 11.07 | 11.80 |
| Glu | 15.82 | 20.21 |
| Gly | 1.92  | 1.95  |
| Pro | 5.98  | 8.96  |
| Ser | 4.70  | 5.10  |

I+ Dialyzable part of whey protein pancreatin hydrolysate (first ultrafiltrate)
II++ Nondialyzable part of whey protein pancreatin hydrolysate (first ultrafiltrate)

The results are expressed in grams per 100 grams of proteins except for the tryptophan (grams per 100 grams of freeze dried powder).

To further characterize the pancreatin hydrolysate it was brought into contact with a cationic resin in the proportion of 7 grams of resin per 100 ml of hydrolysate having a peptide content of 36 g/l. They were maintained in contact for two hours at ambient temperature and different pHs.

Figure 11A:
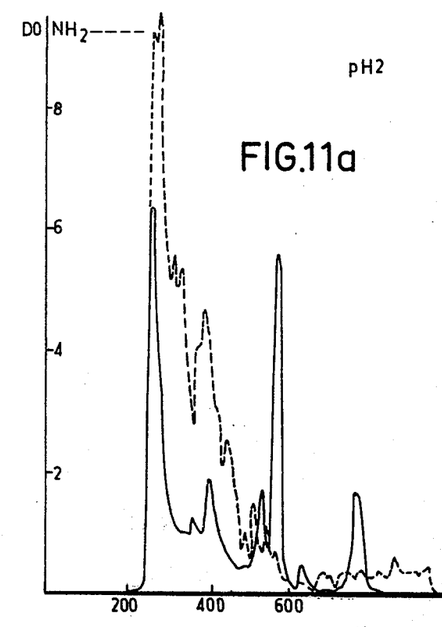
Figure 11B:
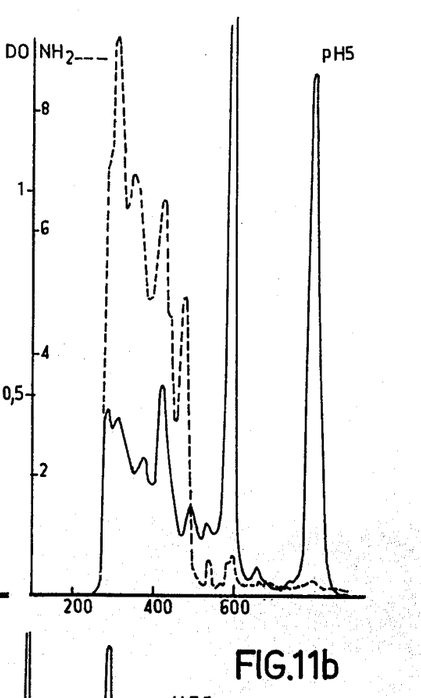
Figure 11C:
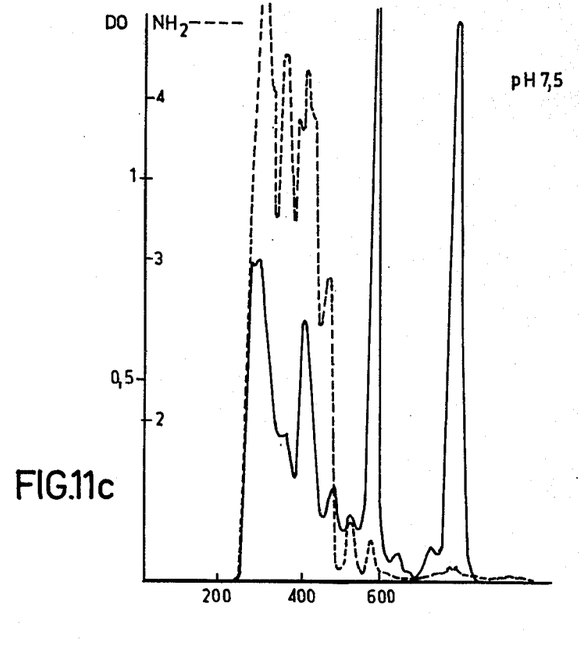
Figure 12:
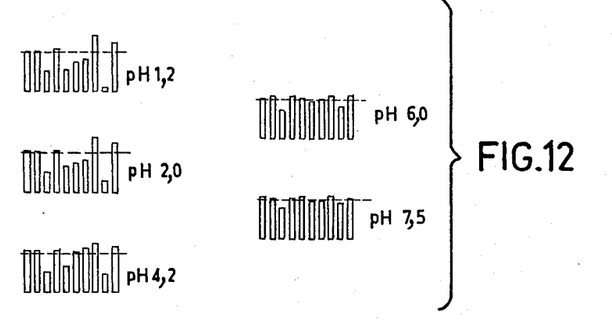

FIGS. 11a, 11b, and 11c show the molecular distribution of the peptides where were not fixed to the cationic resin contained in the various floating portions at pH 2, pH 5 and pH 7.5 respectively. The bar graphs shown in FIG. 12 indicate their essential amino acid composition (expressed as a percentage of the initial hydrolysate). The sequence of the amino acids in the bar graphs is from left to right: Ile, Leu, Lys, Met, Cys, Phe, Tyr, Thr, Trp and Val.

It is observed that the binding of the peptides differs depending on the pH of the reaction. At pH 2 the small peptides and free amino acids preferentially bind themselves to the largest. The latter are weak in lysine, cysteine, tyrosine, phenylalanine and tryptophane. As the pH comes near neutral, the binding of nitrogen diminished. At a pH of 7.5 the amino acid composition of the floating portion is very close to that of the initial hydrolysate.

These various results show that fractionation of the hydrolysate is possible according to this technique. By varying the pH of the reaction, the nature of the resins, their concentration, it is possible to obtain peptidic fractions with precise characteristics.

Figure 13:
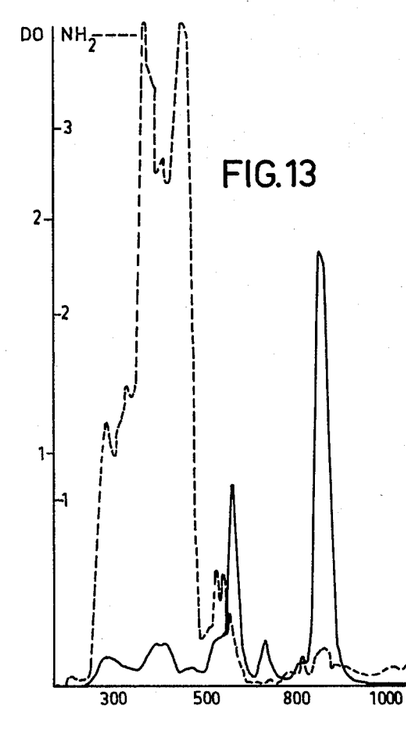
Figure 14:
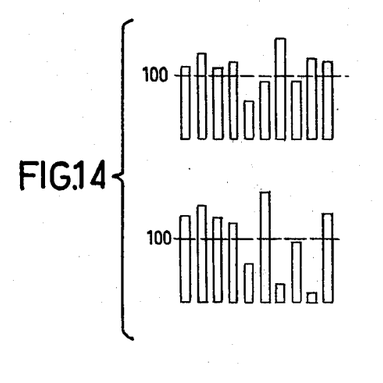

Other experiments were carried out by ultrafiltrating the total hydrolysate across membranes having a cut-off threshold equal to about 2,000 which are capable of partially retaining peptides having a molecular weight greater than 1,500. FIG. 13 illustrates the molecular distribution of the peptides and free amino acids contained in the fraction which permeates through the 2,000 cut-off membrane (Sephadex G 15 gel, 30% acetic acid). Ther permeate fraction of the pancreatin hydrolysate is weak in cysteine and enriched in phenylalanine, tryptophane with respect to the original hydrolysate. FIG. 14 illustrates the essential amino acid composition (expressed as a percentage of their content in the initial hydrolysate), peptides and free amino acids contained in the fraction permeates through the 2,000 cut-off membrane.

EXAMPLE 4

We operated under conditions similar to those of Examples 2 and 3. The peptidic hydrolysate was concentrated then dried. The powder had the properties defined hereinbelow:

| Chemical analysis  | 100 g   |
|--------------------|---------|
| Solid content      | 96.3    |
| Total nitrogenous  | 72.0+   |
| material           | 74.2++  |
|                    | 76.6+++ |
| Ash                | 11.0    |
| Reducing sugars    | 0       |
| Fats               | 0       |
| Minerals           |         |
| Ca                 | 0.94    |
| Na                 | 0.30    |
| K                  | 4.1     |

The analysis of the nitrogen content was carried by a microkjeldhal. The powder was diluted in:
+2% sodium citrate
++0.5 N NaOH
+++distilled water.

The results were expressed in nitrogen×6.38 precipitation with 12% TCA: nil.
amount of NPN floating on N/100 power: 11 g.

| Aminogram |     |     |      |
|-----------|-----|-----|------|
| Ile       | 6.0 | Arg | 2.7  |
| Leu       | 9.9 | His | 1.7  |
| Lys       | 9.2 | Ala | 4.9  |
| Cys       | 1.8 | Asp | 9.5  |
| Phe       | 3.2 | Glu | 17.6 |
| Thr       | 6.7 | Gly | 1.7  |
| Tyr       | 3.6 | Pro | 6.2  |
| Trp       | 2.0 | Ser | 5.5  |
| Val       | 5.5 | Met | 2.0  |

The Examples which follow illustrate the application of the products of the invention to compositions for intensive care foods.

EXAMPLE 5

This example is concerned with an intensive care product usable via the enteral tract on patients requiring a protein intake of the order of 7–12% total caloric intake. Such a products fulfills nutritional requirements in the case of mucoviscidosis or cystic fibrosis of the pancreas, kidney insufficiencies as well as for patients suffering from an infection or inflammatory of the intestinal wall. These proteins are preferred supplied in predigested form.

An appropriate centesimal composition is the following:

| peptidic hydrolysate according to the invention | | 2.50 g |
|---|---|---|
| lipides: | | |
| a mixture of equal parts of: | | |
| butter oil | 0.5 g | |
| T.C.M. | 0.5 g | |
| corn oil | 0.5 g | 4.10 g |
| sunflower oil | 0.5 g | |
| glycerol monostearate | 2.1 g | |
| glucides: | | |
| glucose polymers | 10 g | |
| glucose | 1.5 g | 13.0 g |
| galactose | 1.5 g | |
| vitamins | | |
| A, D, E, B$_1$, B$_2$, PP, B$_5$, B$_6$, B$_{12}$, folic acid, biotin, vitamin C | | according to FA0/WHO |

| -continued | |
|---|---|
| mineral elements | |
| (calcium, sodium, potassium manganese, phosphorus, zinc, iron, copper, magnesium, chlorine, iodine) | 0.455 g |
| distilled water | q.s.p. 100 |

EXAMPLE 6

This example is concerned with an intensive care product usable via the enteral tract on patients requiring a protein intake of the order of 25% of the total caloric intake in predigested form and with a small lipidic intake. This may be the case with considerable tissue destruction after serious traumas or burns.

An appropriate centesimal composition is the following:

| peptidic hydrolysate according to the invention | | 8 g |
|---|---|---|
| lipides: | | |
| T.C.M. | 2.30 g | |
| oil very rich in essential fat acids | 0.50 g | 2.90 g |
| emulsifier | 0.10 g | |
| glucides: | | |
| small glucose polymers | 12.7 g | |
| glucose | 3 g | 18.7 g |
| galactose | 3 g | |
| vitamins | | |
| A, D, E, B$_1$, B$_2$, PP, B$_5$, B$_6$, B$_{12}$, folic acid, biotin, vitamin C | | according to FAO/WHO recommendations |
| minerals: | | |
| (calcium, sodium, potassium, phosphorus, zinc, iron, copper, manganese, chlorine, iodine) | | 0.455 g |
| distilled water | | q.s.p. 100 |

EXAMPLE 7

This example illustrates the preparations of pharmaceutical compositions to be taken orally. Pills were prepared in the usual manner from the following formulation:

| peptidic hydrolysate according to the invention | 200 mg |
|---|---|
| QS excipient for the pill finished at | 300 mg |

The excipient used was talc, magnesium stearate or silica available commercially under the trade name "aerosil".

In the same manner capsules containing 100 mg of peptidic hydrolysate according to the invention and a customary QS excipient for the capsule which finished at 200 mg, were prepared.

Of course the invention is not limited to the above described modes and embodiments. Various modifications may be introduced without departing from the scope of the invention. Thus, a multitude of formulations containg the products according to the invention may be prepared for the most varied nutritional uses.

What we claim is:

1. A total enzymatic hydrolysate from whey proteins comprising a peptidic hydrolysate containing substantially no residual proteins, at least 50% of the peptides of the peptidic hydrolysate containing 2 to 5 amino acids, the amount of free amino acids being less than 15%.

2. A hydrolysate according to claim 1, wherein 70 to 90% of the nitrogen present is in the form of peptides having a number of amino acids less than 10.

3. A hydrolysate according to claim 1 or 2, containing no fraction precipitable in 12% trichloroacetic acid and having the following aminogram:

| Ile | 6.0 | Arg | 2.7 |
|---|---|---|---|
| Leu | 9.9 | His | 1.7 |
| Lys | 9.2 | Ala | 4.9 |
| Cys | 1.8 | Asp | 9.5 |
| Phe | 3.2 | Glu | 17.6 |
| Thr | 6.7 | Gly | 1.7 |
| Tyr | 3.6 | Pro | 6.2 |
| Trp | 2.0 | Ser | 5.5 |
| Val | 5.5 | Met | 2.0. |

4. A food or food supplement comprising the total enzymatic hydrolysate according to claim 1 adapted for specific nutrition requirements.

5. A diet food comprising the total enzymatic hydrolysate according to claim 1 in combination with a neutral vehicle for oral or enteral feeding.

6. An intensive care food comprising the total enzymatic hydrolysate according to claim 1 in combination with a neutral vehicle suitable for oral or enteral feeding.

7. A product for therapeutic nutrition containing the total enzymatic hydrolysate according to claim 1.

8. A medicine comprising the total enzymatic hydrolysate according to claim 1.

9. A pharmaceutical composition comprising the total enzymatic hydrolysate according to claim 1 in combination with a neutral carrier suitable for oral or enteral administration.

* * * * *